(12) United States Patent
Madsen et al.

(10) Patent No.: US 10,864,457 B2
(45) Date of Patent: Dec. 15, 2020

(54) SPRAY FREEZING

(71) Applicant: CHR. HANSEN A/S, Hoersholm (DK)

(72) Inventors: Michelle Madsen, Kirke Hyllinge (DK); Allan Jensen, Hedehusene (DK); Hans Bisgaard-Frantzen, Roedovre (DK)

(73) Assignee: CHR. HANSEN A/S, Hoersholm (DK)

( * ) Notice: Subject to any disclaimer, the term of this patent is extended or adjusted under 35 U.S.C. 154(b) by 0 days.

(21) Appl. No.: 15/529,317

(22) PCT Filed: Nov. 30, 2015

(86) PCT No.: PCT/EP2015/078073
§ 371 (c)(1),
(2) Date: May 24, 2017

(87) PCT Pub. No.: WO2016/083617
PCT Pub. Date: Jun. 2, 2016

(65) Prior Publication Data
US 2017/0259185 A1 Sep. 14, 2017

(30) Foreign Application Priority Data
Nov. 28, 2014 (DK) .................................. 2014 00697

(51) Int. Cl.
| | |
|---|---|
| *C12N 1/04* | (2006.01) |
| *B01D 1/16* | (2006.01) |
| *C12M 1/00* | (2006.01) |
| *C12N 1/20* | (2006.01) |
| *B05B 17/00* | (2006.01) |
| *F26B 5/06* | (2006.01) |

(52) U.S. Cl.
CPC ............... *B01D 1/16* (2013.01); *B05B 17/00* (2013.01); *C12M 45/22* (2013.01); *C12M 47/14* (2013.01); *C12N 1/04* (2013.01); *C12N 1/20* (2013.01); *F26B 5/06* (2013.01)

(58) Field of Classification Search
None
See application file for complete search history.

(56) References Cited

U.S. PATENT DOCUMENTS

| | | | |
|---|---|---|---|
| 6,010,725 A | | 1/2000 | Meister et al. |
| 7,007,406 B2 | | 3/2006 | Wang et al. |
| 2010/0011610 A1 * | | 1/2010 | Bittorf .................... F26B 3/08 34/359 |

FOREIGN PATENT DOCUMENTS

| | | |
|---|---|---|
| CN | 102226629 A | 10/2011 |
| EP | 1 234 019 B1 | 9/2009 |
| WO | WO 2005/061088 A1 | 7/2005 |
| WO | WO 2014/029758 A1 | 2/2014 |
| WO | WO 2014/029783 A1 | 2/2014 |
| WO | WO 2015/063090 A2 | 5/2015 |

OTHER PUBLICATIONS

Corning, Technical Bulletin, General Guide for Cryogenically Storing Animal Cell Cultures, retrieved from the internet (Jan. 28, 2019): https://www.corning.com/media/worldwide/cls/documents/t_cryoanimalcc.pdf.*
Lievense et al., The Inactivation of Lactobacillus Plantarum During Drying, Chapter 1, General Introduction, pp. 1-11, 1991.*
Manu et al., Research J. Pharma. Dosage Forms and Tech., 2011; 4(2): 74-79.*
Rajam et al., LWT—Food Science and Technology vol. 60 (2015), pp. 773-780; published online Oct. 7, 2014.*
Al-Hakim et al., An investigation of spray-freezing and spray-freeze-dryings, Doctoral Thesis, Loughborough University, 2004.*
Rajam et al, Journal of Food Engineering, 2015, vol. 166, pp. 95-103 (Year: 2015).*
U.S. Appl. No. 15/031,591, Madsen et al. To be issued as U.S. Pat. No. 10,745,661 on Aug. 18, 2020. (Year: 2020).*
ISO 13320 "Particle size analysis—Laser diffraction methods," International Organization for Standardization, (2009), Reference No. ISO 13320:2009(E).
Chavez et al., "Drying of Probiotics: Optimization of Formulation and Process to Enhance Storage Survival," *Drying Technology*, vol. 25, pp. 1193-1201 (Jul. 2007).
Meng et al., "Anhydrobiotics: The challenges of drying probiotic cultures," *Food Chemistry*, vol. 106, pp. 1406-1416 (2008) (available Oct. 2007).
Madhu, et al., "Impact of Freeze and Spray Drying on the Retention of Probiotic Properties of *Lactobacillus fermentum*: An in vitro Evaluation Model," *International Journal of Microbiological Research*, vol. 2, No. 3, pp. 243-251 (2011).
Peighambardoust, et al., "Application of spray drying for preservation of lactic acid starter cultures: a review," *Trends in Food Science & Technology*, vol. 22, pp. 215-224 (Feb. 2011).
Dolly, et al., "Microencapsulation of Lactobacillus Plantarum (mtcc 5422) by spray-freeze-drying method and evaluation of survival in simulated gastrointestinal conditions," *Journal of Microencapsulation*, vol. 28, No. 6, pp. 568-574 (Aug. 2011).
Semyonov, et al., "Microencapsutation of *Lactobacillus paracasei* by spray freeze drying," *Food Research International*, vol. 43, pp. 193-202 (Jan. 2010).
Santivarangkna et al., "Alternative Drying Processes for the Industrial Preservation of Lactic Acid Starter Cultures," *Biotechnol. Prog.*, vol. 23, pp. 302-315 (Apr. 2007).
International Search Report and Written Opinion issued in International Patent Application No. PCT/EP2015/078073, completed Feb. 16, 2016.

* cited by examiner

*Primary Examiner* — Allison M Fox
(74) *Attorney, Agent, or Firm* — Foley & Lardner LLP

(57) ABSTRACT

The present invention relates to an improved method for preservation of e.g. microorganisms, especially lactic acid bacteria, said method includes spray freezing.

26 Claims, 5 Drawing Sheets

(a) Inert gas supply
(b) Inert gas heater
(c) Inlet temperature control loop
(d) Combined spray drying/freezing chamber
(e) Liquid feed supply
(f) Liquid feed pump
(g) Atomizer
(h) Cyclone
(i) Warm water scrubber (j) Exhaust fan
(k) Chamber pressure control loop
(l) Outlet temperature control loop
(m) Powder discharge
(y) cryogenic gas inlet

SPRAY FREEZING

CROSS-REFERENCE TO RELATED APPLICATIONS

The present application is the U.S. National Stage of International Application PCT/EP2015/078073, filed Nov. 30, 2015, and claims priority to Denmark Patent Application No. PA 2014 00697, filed Nov. 28, 2014

FIELD OF INVENTION

The present invention relates to an improved method for drying and/or freezing proteins or microorganisms, especially lactic acid bacteria, said method includes spraying of a suspension/solution of the protein or microorganism into a gas.

BACKGROUND OF INVENTION

Spray drying has previously been used for drying lactic acid bacteria, but without much commercial success. For instance U.S. Pat. No. 6,010,725A (Nestle) relates to a process for spray drying microorganisms in a spray drying apparatus having an inlet temperature above 250 Degrees Centigrade (° C.). It is stated that at least 10% of the microorganisms survive the treatment.

Spray freezing has recently been proposed for freezing lactic acid bacteria, but with limited commercial success. Semyonov et al (Food Research International 43, 193-202 (2010) have investigated the survival of *Lactobacillus paracasei* cells which were microencapsulated by "spray freeze drying", i.e. spray freezing succeeded by freeze drying. Apparently, the bacterial suspension is sprayed directly into nitrogen in its liquid state, which process results in microcapsules having as size distribution between 400 and 1800 micrometers (microns). It is concluded that bulk freeze drying resulted in slightly higher survival than spray freeze drying, and that particles having a size about 1000-1400 micrometer result in a higher survival than 400 micrometer particles.

U.S. Pat. No. 7,007,406 (Wang) discloses a spray-freezing apparatus, where the frozen product is collected on a filter.

All the above spray freezing and drying processes have had limited commercial success, especially when the product to be preserved is bacteria cells which should be viable after thawing or rehydrating.

SUMMARY OF INVENTION

The present inventors have surprisingly discovered that bacteria cells can be preserved very effectively and with a high survival rate by a process which includes spray freezing, if:
  the spray freezing step is preceded by a drying step, wherein the atomized particles are (partly) dried by contacting with a drying gas;
  the freezing is carried out by freezing the atomized particles in a cryogenic gas; and/or
  the frozen product is collected by means of a cyclone.

Also, the present inventors have observed that the freezing process of the invention has unexpected advantages compared to the traditional freezing processes, such as:

- improved process economy due to i) less consumption of nitrogen gas for freezing, compared to pellet freezing, ii) it is possible to operate a freeze-dryer more efficiently with a frozen product obtained by the present invention, calculated by the amount loaded into the freeze dryer, and amount of the final product obtained after the freeze drying, and iii) a more compact frozen product is obtained, thereby reducing the need for freezer space and/or easier transport, and
- improved removal of liquid if the suspension/solution is subjected to a pre-drying step before the freezing step; apparently the evaporated liquid does not form particles in the freezing step and is removed together with the cryogenic gas, and/or any formed particles are so small that they are separated from the desired frozen product, e.g. in a cyclone.

In more details, the present inventors have shown that in conventional spray freezing of aqueous formulations at ambient atmospheric pressure using liquid nitrogen and/or very cold nitrogen gas, no drying takes place during the freezing process at all, thus only offering a smaller particulate for downstream freeze drying compared to the larger pellets obtained conventional pelletizing in liquid nitrogen. Conventionally, spray dryers have throughput rates so low that these drying methods do not offer an economical feasible alternative to for example freeze drying. Too high dryer outlet temperatures will destroy and kill most lactic acid bacteria strains efficiently, as most bacteria living in the human gut (such as lactic acid bacteria—hereafter abbreviated LAB, especially anaerobic LAB) will not survive 40° C. for much time.

In an attempt to combine spray drying and downstream freezing of the partially dehydrated droplets, the present inventors retrofitted a heated (nitrogen) gas distributor around the atomization device placed at the top of a spray freezing chamber. The spray freezing chamber was modified so the upper half would sustain temperatures well above the freezing point of most aqueous LAB suspensions and in the lower half of the combined spray drying/freezing chamber, liquid nitrogen was injected in order to accomplish spray freezing of the partially dehydrated droplets generated by the atomization device in the top of the chamber.

After freezing, the microscopic ice crystals and the much larger frozen product pellets was pneumatically transported to a downstream cyclone by the combined amounts of nitrogen gas from both the spray drying and downstream spray freezing sections of the spray chamber. The microscopic ice crystals was so small the downstream cyclone separator was not be able to separate them completely from the nitrogen gas, whereas the much larger frozen product pellets was efficiently be separated from the nitrogen gas as expected. Thus, it has surprisingly turned out that it is advantageous to use a cyclone for separation of the frozen particles from the cryogenic gas. The present inventors discovered that any water vapour from the initial spray drying process will shock freeze into microscopic ice crystals along with freezing of the partially dehydrated droplets arriving from the upper warm half of the spray chamber almost instantly upon contact with the liquid nitrogen spray in the lower half of the spray chamber. The recovered partially dehydrated/frozen product pellets (in various sizes in the range 50 to 400 microns) typically displayed a decrease in moisture content in the range of 0.5-50% (w/w), depending on drying gas rate/temperature and product feed rate and was found to have approx. 15% higher bulk density compared to the much larger commercially available frozen product pellets (3000-10000 microns or 3-10 mm), generated by conventional liquid nitrogen pelletizing, thus increasing the overall capacity of any freeze dryer unit used for the downstream final drying step of the product.

The inventors continued their investigations, and performed downstream final freeze drying of the recovered partially dehydrated/frozen product pellets and found the new invention which combines spray drying/freezing process yields surprisingly high bacterial survival and activity after drying.

To their surprise, they also found the freeze dried micropellets shrink substantially compared to freeze dried larger frozen product pellets, generated by conventional liquid nitrogen pelletizing, in fact the final bulk density of the freeze dried product was about 2½ times higher than conventional freeze dried powders. The density increase translates into much lower product porosity and thus improved product stability and many other advantages in the final application of the product.

The present inventors discovered that the best result was obtained when the drying gas used in spray dryer/freezer was free of oxygen, and we therefore contemplate that the gas should preferably be an inert gas like Nitrogen or any noble gas like Helium, Argon and Neon etc. The best result is presently obtained by combining the use of an inert drying/cryogenic/conveying gas with drying pressures at ambient pressure, but it is contemplated that it will be an advantage to carry out the process at pressures below or above ambient pressure.

The spray drying/freezing method of the invention results in improved survival and stability of the LAB, and combined with the dryness of the produced LAB containing powders this yields an economical feasible pre-drying/freezing process for heat- and oxygen labile LAB containing products.

Further, it has turned out that the product of the combined drying/freezing process followed by conventional freeze drying, i.e. the dried powder, has several unexpected advantages relative to freeze dried much larger frozen product pellets, generated by conventional liquid nitrogen pelletizing, containing the same heat-labile material, e.g. improved survival (more active material, i.e. higher yield), easier applicability (the powder is easier to disperse in an aqueous solution or suspension, such as milk).

The invention does not limit itself for LAB drying alone: Most live bacterial/viral strains, large macro-molecules like proteins/peptides and other biopharmaceutical/biological products in general will benefit from this oxygen-free and low temperature pre-drying/freezing method. Thus, the present invention comprises these embodiments.

In accordance with the above surprising findings, the present invention in a first aspect relates to a process for preserving heat labile material such as proteins or microorganisms by freezing and optionally drying a solution or suspension containing the material, characterized by contacting droplets of the suspension or solution with a drying gas and subsequent contacting the (partially) dried droplets with a cryogenic gas.

In a second aspect, the present invention relates to a product obtainable by the process of the first aspect.

In a third aspect, the present invention relates to an apparatus usable in the process of the first aspect, such as an apparatus comprising a chamber with i) an atomizing means for atomizing the suspension, ii) an inlet for a drying gas (optionally integrated in the atomizing means), iii) an inlet for a cryogenic gas, and iv) an outlet optionally connected with a cyclone, e.g. an apparatus substantially as depicted on FIG. 1 or 4.

DETAILED DISCLOSURE

In a first aspect, the present invention relates to a process for preserving (freezing and/or drying) microorganisms (esp. LAB (Lactic Acid Bacteria)) or proteins, said process involves subjecting droplets (e.g. an atomized suspension) containing the microorganism/protein to a cryogenic gas. Interesting embodiments of this first aspect are:

1: A process for preserving microorganisms (esp. LAB (Lactic Acid Bacteria)), such as preserving by freezing and optionally drying, comprising the following steps:
  a) Preparing droplets (preferably having a size from 10 to 500 micrometer, such as a size in the ranges: 15 to 400, 20 to 350, 50 to 350, 100 to 350, 20 to 300, 20 to 200, 50 to 300, 50 to 200, 100 to 300, or 100 to 200, measured as the Dv90 value (Dv90 is defined as the maximum particle diameter below which 90% of sample volume exists, according to the ISO 13320: 2009 standard for *Particle size analysis—Laser diffraction methods*, measured in micrometer)) of an aqueous (or liquid) suspension containing the microorganisms (preferably having a content of at least 1.0E+8 microorganisms per ml), e.g. by spraying (atomizing) the suspension; and
  b) Optionally contacting the droplets with a drying gas (preferably having a temperature in the range from 20° C. to 250° C., and/or preferably for a time period of from 1 second to 120 seconds); and
  c) Contacting the droplets, such as the droplets resulting from the preceding step, with a cryogenic gas (preferably having an temperature in the range from −20 to −150° C. or from −50 to −100° C., and/or preferably for a time period of from 1 sec to 120 sec); and
  d) optionally subjecting the resulting frozen product from the preceding step to a further drying step, such as drying under reduced pressure, e.g. freeze-drying; and
  e) optionally packaging the microorganisms, such as in an air-tight and/or moisture-tight package (optionally together with microorganisms of a different strain).

2: A process for drying a microorganism (esp. a LAB) containing suspension, characterized in that:
  i) an aqueous suspension containing microorganisms (preferably having a concentration of at least 1.0E+8 microorganisms per ml) is sprayed into a cryogenic gas (preferably having a temperature in the range from −20 to −150° C.) in a spray chamber; and
  ii) the frozen product from step a) is collected and freeze dried until a water activity of less than 0.20 is achieved.

3: A process for drying a microorganism (esp. a LAB) containing suspension, characterized in that:
  i) an aqueous suspension containing microorganisms (preferably having a concentration of at least 1.0E+8 microorganisms per ml) is sprayed into a drying gas (preferably having a temperature in the range from 30 to 200° C.) in a spray chamber;
  ii) the product from step a1) is contacted with a cryogenic gas (preferably having a temperature in the range from −20 to −150° C.) in a chamber; and
  iii) the frozen powder from step a) is collected and freeze dried until a water activity of less than 0.20 is achieved.

4: A process for drying (or removing liquid from) a solution or suspension containing proteins (such as enzymes, hormones, human proteins, therapeutically active proteins or lipoproteins) or microorganisms (such as bacteria, LAB, yeasts, fungi, plant cells, animal cells, or vira), characterized by:
  a) Preparing droplets (preferably having a size from 10 to 500 micrometer, such as a size in the ranges: 15 to 400, 20 to 350, 50 to 350, 100 to 350, 20 to 300, 20 to 200, 50 to 300, 50 to 200, 100 to 300, or 100 to 200, measured as Dv90 in microns) of the suspension or solution, e.g. by spraying the solution or suspension; and b) Optionally contacting the droplets with a drying gas (preferably having a temperature in the range from 20 degrees C. to 250 degrees C., and/or preferably for a time period of from 1 second to 120 seconds); and c) Contacting the droplets obtained in step a) or b) with a cryogenic gas (preferably having an temperature in the range from −20 to −150 degrees C. or from −50 to −100, and/or preferably for a time period of from 1 sec to 120 sec); and d) subjecting the resulting frozen product from the preceding step to a further drying step, such as drying under reduced pressure, e.g. freeze-drying; and e) Optionally packaging the product, such as in an air-tight and/or moisture-tight package.

5: A process for freezing a suspension containing microorganisms (esp. LAB), by:

Spraying the suspension into a chamber containing a drying gas (preferably having a temperature in the range from 20 degrees C. to 250 degrees C., and/or preferably so the suspension is in contact with the gas for a time period of from 1 second to 120 seconds); and Freezing the product from the preceding step by contacting with a cryogenic gas in a (preferably having an temperature in the range from −20 to −150 degrees C. or from −50 to −100, and/or preferably so the product is in contact with the cryogenic gas for a time period of from 1 sec to 120 sec); and optionally packaging the frozen suspension, such as in an air-tight and/or moisture-tight package.

It the above processes, it should be understood that the drying step is performed for a time sufficient for achieving the desired degree of drying, and the freezing is performed for a time sufficient for a complete freezing can be achieved, i.e. the product should be completely frozen. The skilled person knows how to obtain the suitable conditions in e.g. a two-chamber (two-zone) spray tower, and he knows how to calculate the height of the spray tower so the sprayed suspension has a suitable passage time through the drying chamber/zone and freezing chamber/zone, resp.

In the above processes, the droplets are preferably prepared by spraying. The spraying may be carried out by means of a spray nozzle (atomizing device), such as an ultrasound nozzle, a pressure nozzle, a two-fluid nozzle (e.g. using N2 as atomizing gas), or a rotating atomizing device, the atomizing preferably resulting in droplets having a size from 10 to 500 micrometer, such as having a size selected from one of the following ranges: 15 to 400, 20 to 350, 50 to 350, 100 to 350, 20 to 300, 20 to 200, 50 to 300, 50 to 200, 100 to 300, or 100 to 200, measured as Dv90 values in micrometer.

The frozen product (e.g. powder) may be collected by means of a cyclone, or an electrostatic filter. A cyclone is presently preferred, such as a cyclone operated with a with a maximum differential pressure drop across the cyclone of 10 mm to 300 mm water column, or 50 to 200 mm water column, or approx. 100 mm water column.

It is presently preferred that the spray drying and/or that the freezing step takes place under a pressure between 60 and 200 kPa, such as between 80 and 150 kPa or between 60 and 120 kPa, between 70 and 110 kPa, or between 105 and 140 kPa.

Advantageously, the final drying step (of the frozen product) may take place under reduced pressure, such as by freeze-drying, preferably to an aw below 0.20.

Other interesting embodiments of the processes of the first aspect are:

A process, wherein the "retention time" is less than 2 minutes in the spray dryer, and preferably the resulting spray-dried (or partly dried) product is directly introduced into a freezing chamber, such as by using an apparatus wherein the dried (or partially dried) product from the spray drying is transferred into the freezing chamber by means of the gravity.

A process, wherein the spray-drying step is carried out at with a drying gas inlet temperature of at most 300° C., advantageously between 20° C. and 250° C. and more preferably between 100° C. and 200° C.

A process, wherein the spray-drying step takes place at a temperature in the range from 20° C. to 200° C., and/or preferably for a time period of from 1 second to 120 seconds).

A process, wherein after the spray-drying step, the droplet has a size of between 20 and 400 microns and preferably between 50 and 300 microns.

A process, wherein after the spray-drying step the water content of the droplet is at least 20 percent by weight reduced compared to the starting suspension, preferably at least 40%, at least 60% or at least 75%.

A process, wherein after the drying step the liquid (e.g. water) content of the droplet is at least 5% by weight reduced compared to the starting suspension/solution, preferably at least 10%.

A process, wherein after the drying step the liquid (e.g. water) content of the droplet is between 20% and 75% by weight, with respect to the total weight of the droplet.

A process, wherein after the spray-drying step the water content of the droplet is between 20% and 85% by weight, (preferably between 30% and 80%, or between 40% and 75% percent by weight), with respect to the total weight of the droplet.

A process, wherein the duration of the freeze-drying step is a time suitable for obtaining a powder whose residual water content of the powder is at least 0.15.

A process, wherein the drying gas contains less than 5% oxygen, such as less than 2%.

A process, wherein the cryogenic gas contains less than 5% oxygen, such as less than 2%.

A process, wherein the drying gas is selected from the group consisting of an inert gas (such as Nitrogen), a noble gas (such as Helium, Argon or Neon) etc., carbon dioxide, and an alkane gas (such methane), and a mixture thereof.

A process, wherein the cryogenic gas is selected from the group consisting of an inert gas (such as Nitrogen), a noble gas (such as Helium, Argon or Neon) etc., carbon dioxide, and an alkane gas (such methane), and a mixture thereof.

A process, wherein the cryogenic gas has (an inlet) temperature in the range from −50 to −250° C. or in the range from −80 to −160° C.

A process, wherein the solution or suspension further comprises an additive that stabilizes the material/microorganism. The additive may be selected from the group consisting of: Inositol, lactose, sucrose, trehalose, inulin, maltodextrin, skimmed milk powder, yeast extract, casein peptone, inosine, inosinemonophospate, monosodium glutaminate, sodium caseinate, and sodium ascorbate, polysorbate. It is presently preferred that the ratio heat labile material (proteins or microorganisms):additive is within the range from 1:0.5 to 1:5, such as from 1:1 to 1:4 or from 1:1½ to 1:3, (w/w of the dry weights).

A process, wherein the microorganism is selected from the group consisting of: a yeast (eg *Saccharomyces*), a lactic acid bacterium, a *Streptococcus* species, a *Lactobacillus* species, a *Lactococcus* species, a *Leuconostoc* species, a *Bifidobacterium* species, an *Oenococcus* species, a *Bacillus* species.

A process, wherein the microorganism is selected from the group consisting of Streptococci species, such as *Streptococcus thermophilus*.

A process, wherein the microorganism is selected from the group consisting of *Bifidobacterium* species, such as *B. animalis* ssp. *lactis* or *B. longum*.

A process, wherein the microorganism is selected from the group consisting of *Lactobacillus* species, such *L. acidophilus* or *L. bulgaricus*.

A process, wherein the microorganism is selected from the group consisting of *Lactococcus* species, such as *L. lactis* or *L. cremoris*

A process, wherein the microorganism is selected from the group consisting of *Bacillus* species, such as *B. subtilis*.

A process, which process takes place in an apparatus according to the invention, such as in an apparatus substantially as depicted in the FIGS. 1, 4, 5, and/or 6.

In a second aspect, the present invention relates to a product obtainable by any of the above processes. In a presently preferred embodiment, the product may be packaged (e.g. in an airtight container).

In a specific embodiment, an additive is added to the heat labile material before spraying, especially if the material is to be subjected to freeze drying. The additive is preferable a mixture of different compounds that protect the material during freezing. A preferred additive comprises 5-50% ascorbic acid (or ascorbate), 5-50% inositol, and 5-50% glutamate (in dry form, w/w). Such an additive is also a part of the present invention.

In a third aspect, the present invention relates to an apparatus usable in any of the above processes, such as an apparatus comprising a chamber with i) an atomizing means for atomizing the suspension, ii) an inlet for a drying gas (optionally integrated in the atomizing means), iii) an inlet for a cryogenic gas, and iv) an outlet optionally connected with a cyclone, e.g. an apparatus substantially as depicted on FIG. 1 or FIG. 4.

An interesting embodiment of the third aspect is an apparatus of the invention, which comprises a two-chamber tower (wherein the first chamber is placed over the second chamber) wherein the first (upper) chamber (11) comprises i) an atomizing means for atomizing the suspension (5), and ii) an inlet for the drying gas (optionally integrated in the atomizing means); and the second (lower) chamber (12) comprises i) an inlet for a cryogenic gas and ii) an outlet coupled to a first cyclone (14). It should be understood that by placing the first chamber over the second chamber, the chambers are linked so that the (partially) dried particles will by means of the gravity drop from the first chamber into the second chamber.

Yet an embodiment relates to an apparatus (such as a spray tower) comprising an first (upper) chamber (11) and a second (lower) chamber (12), wherein the upper chamber comprises means for atomizing a suspension or solution (5); and
an inlet for a drying gas (1), and
means (3) for heating the drying gas to a temperature in the range 20° C. to 250° C.; and wherein the lower chamber comprises
an inlet for a cryogenic gas (4) (adapted for a gas having a temperature in the range −50 to −250° C.) and optionally a tank for storing the cryogenic gas; and
an outlet for the frozen product, said outlet being connected to a cyclone (13); and wherein the upper chamber is placed so the (partly) dried particles drop into the lower chamber for subsequent freezing.

An interesting embodiment is an apparatus, such as an apparatus according to the preceding embodiment, comprising a first (upper) chamber and a second (lower) chamber, wherein the upper chamber comprises means for atomizing a suspension or solution; and
means of injection of drying gas; and
means for supplying the drying gas at a temperature in the range 20° C. to 250° C.;

And wherein the lower chamber comprises means for injection of a cryogenic gas; and
means for supplying the cryogenic gas at a temperature in the range −50 to −250° C.; and
an outlet for the frozen product, said outlet preferably being connected to a cyclone.

In a presently preferred embodiment, first chamber is connected to a heater for heating the drying gas. It is also preferred that the second chamber is connected to a tank adapted to a cryogenic gas.

In case the apparatus should be operated at a pressure different from ambient pressure, the apparatus should comprises means for lowering the pressure (e.g. to a pressure below 0.9 bar) in the first chamber and/or in the second chamber, or means for increasing the pressure (e.g. to a pressure above 1.1 bar) in the first chamber and/or in the second chamber.

It is presently preferred that the first chamber has a height that allows at least 5% of the liquid in the suspension/solution to evaporate during the passage, and wherein the second chamber has a height that allows a complete freezing of the product entering from the upper chamber. In an embodiment, the first chamber is essential cylindrical and has a diameter of 0.5 to 5 m and a height of 1 to 4 times the diameter. In yet an embodiment, the second chamber is essential cylindrical and has a diameter of 0.5 to 5 m and a height of 1 to 2 times the diameter. In an preferred embodiment, the first and second chamber is connected so the first chamber is the upper part of and the second chamber is the lower part of an essential cylindrical structure which and has a diameter of 0.5 to 5 m and a total height of 2 to 6 times the diameter.

The apparatus may further comprise a second cyclone coupled to the material outlet of the first cyclone. Advantageously, the apparatus of the invention further comprises a gas inlet between the first cyclone and the second cyclone, so that the gas will convey the material discharged from the first cyclone to the second cyclone. The gas may be a cryogenic gas, and/or a gas which contains less than 5% oxygen, such as less than 2%. The gas may be selected from the group consisting of an inert gas (such as Nitrogen), a noble gas (such as Helium, Argon or Neon) etc., carbon dioxide, and an alkane gas (such methane), and a mixture thereof.

In a preferred embodiment, the following apparatus is used as described, cf. FIG. 1:

A primary inert gas supply (a) is connected to the inlet of a gas heater (b). The gas heater is connected to the combined spray drying/freezing chamber top inlet (d) and heats the inert gas to an the inlet temperature set by the inlet control loop (c).

The liquid feed supply (e) is connected to the suction side of a liquid feed pump (f) which pumps the liquid formulation to the atomization device (g) on the top of the combined spray drying/freezing chamber (d). The atomization device (g) sprays the liquid feed into a cloud of aerosol droplets which dries into partially dehydrates droplets by consuming the heat supplied by the heated inert gas.

As the partially dehydrated droplets leaves the upper warm section of the combined spray drying/freezing chamber (d) together with the now cooled and moist inert gas, both rapidly cools down as they enter the liquid nitrogen cooled lower section of the combined spray drying/freezing chamber (d). Cold nitrogen gas pulls microscopic water crystals and now frozen partially dehydrated product towards the chamber outlet and pneumatically transports the particulates towards a downstream cyclone separator (h) where the frozen partially dehydrated particles are separated from the inert gas and microscopic ice crystals. The cold and inert gas and microscopic ice crystals are led to a warm water scrubber unit (i) and downstream an exhaust fan (j) creates the required chamber pressure set by the chamber pressure control loop (k). To improve the control of the combined drying/freeze chamber outlet temperature an outlet temperature control loop (l) is used to control the liquid nitrogen injection (y).

In a last aspect, the invention relates to the use of the apparatus of the invention, wherein a drying gas (having a temperature in the range 20° C. to 250° C.) and a liquid containing a protein or a microorganism is sprayed into the upper chamber; and a cryogenic gas (having a temperature in the range −50 to −250° C.) is sprayed into the lower chamber.

Definitions

As used herein, the term "lactic acid bacterium" (LAB) designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Additionally, lactic acid producing bacteria belonging to the group of the strict anaerobic bacteria, bifidobacteria, i.e. *Bifidobacterium* spp., are generally included in the group of lactic acid bacteria. These are frequently used as food cultures alone or in combination with other lactic acid bacteria. Interesting species of LAB are selected from the group comprising the strains of the species and subspecies *Bifidobacterium bifidum, Bifidobacterium lactis, Bifidobacterium longum, Bifidobacterium breve, Bifidobacterium animalis* ssp. *lactis, Lactobacillus reuteri, Lactobacillus acidophilus, Lactobacillus casei, Lactobacillus plantarum, Lactobacillus delbruckii bulgaricus, Lactobacillus rhamnosus, Streptococcus thermophilus, Streptococcus salivarius, Lactococcus lactis, Lactobacillus pentoceus, Lactobacillus buchneri, Lactobacillus brevis, Pediococcus pentosaceus, Pediococcus acidilactici, Pediococcus pervulus, Propionibacterium freudenreichi, Propionibacterium jenseni* and mixtures thereof.

Also the term LAB includes the strains *Lactobacillus rhamnosus* GG (LGG), *Lactobacillus casei* (LC-431), *Lactococcus lactis* (R704), *Bifidobacterium animalis* ssp. *Lactis* (BB-12), *Streptococcus thermophilus* (ST-Fe 2), *Lactobacillus bulgaricus* (LB CH-2)

In the present context, the term "spray drying" means partially removing liquid (e.g. water) from a solution or suspension, i.e. a concentration of the desired microorganism or protein containing solution/suspension. In the spray drying process of the invention, it is presently preferred that 10% to 70% of the water in the droplet is removed, and/or the ratio of dry heat labile material in the product (microorganism/protein) after spray drying has increased more than 25% but less than 400% (compared to the ratio of the starting material). Thus, the product after the spray drying is preferably a liquid or a wet product, and not a dry powder. Presently preferred is a liquid (e.g. aqueous) suspension with a microorganism, or a liquid (e.g. aqueous) solution with a protein. By not drying the product completely, less heat labile material is inactivated. The skilled person knows how to secure that the material is not inactivated, e.g. by lowering the temperature of the drying gas, and/or reducing the contact time with the drying gas, and/or by reducing the distance the droplets have to travel in the spray drying chamber.

If the product after spray freezing is subjected to freeze drying, it is presently preferred that the water activity (aw) of the resulting product is below 0.2.

In the present context, the term "packaging" (a suitable amount of) the frozen or dried microorganism in a suitable packaging relates to the final packaging to obtain a product that can be shipped to a customer. A suitable packaging may thus be a container, bottle or similar, and a suitable amount may be e.g. 1 g to 30000 g, but it is presently preferred that the amount of the microorganism in a package is from 50 g to 10000 g.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

FIGURES

FIG. 1 depicts a preferred spray drying equipment that can be used according to the invention.

(a) drying gas supply
(b) drying gas heater
(c) Inlet temperature control loop
(d) Combined spray drying/freezing chamber
(e) Liquid feed supply
(f) Liquid feed pump
(g) Atomization device
(h) Cyclone separator
(i) Warm water scrubber unit
(j) Exhaust fan
(k) Chamber pressure control loop
(l) Outlet temperature control loop
(m) powder discharge
(y) cryogenic gas inlet FIG. 2 depicts the stability data for the strain ST-44 after 3 months storage at −20° C. and at +5° C., cf. example 4.

Figure 5:
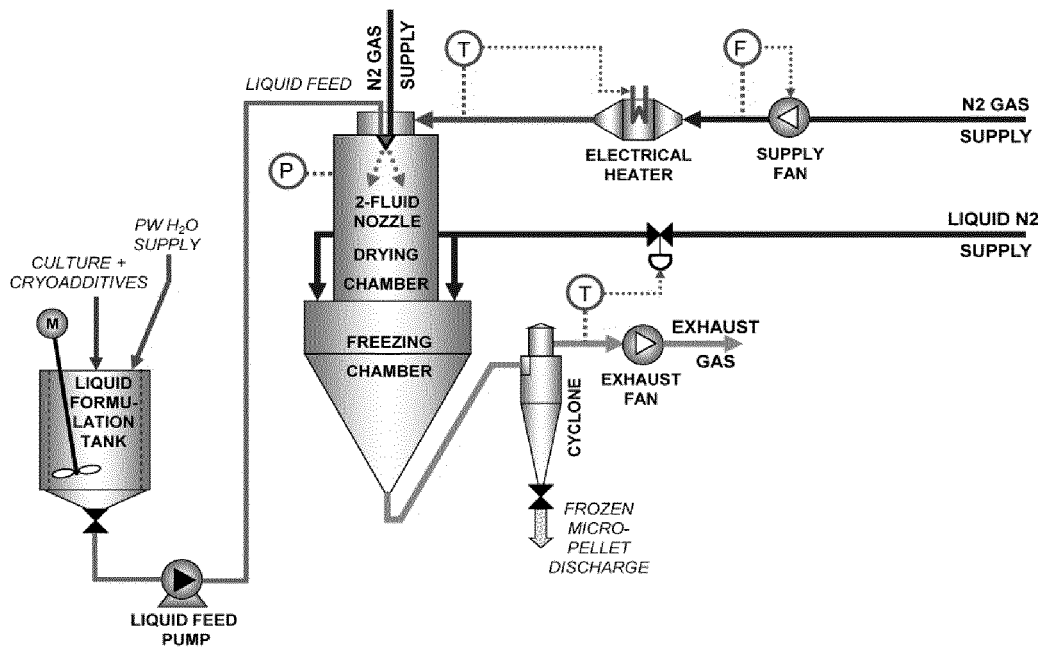
Figure 6:
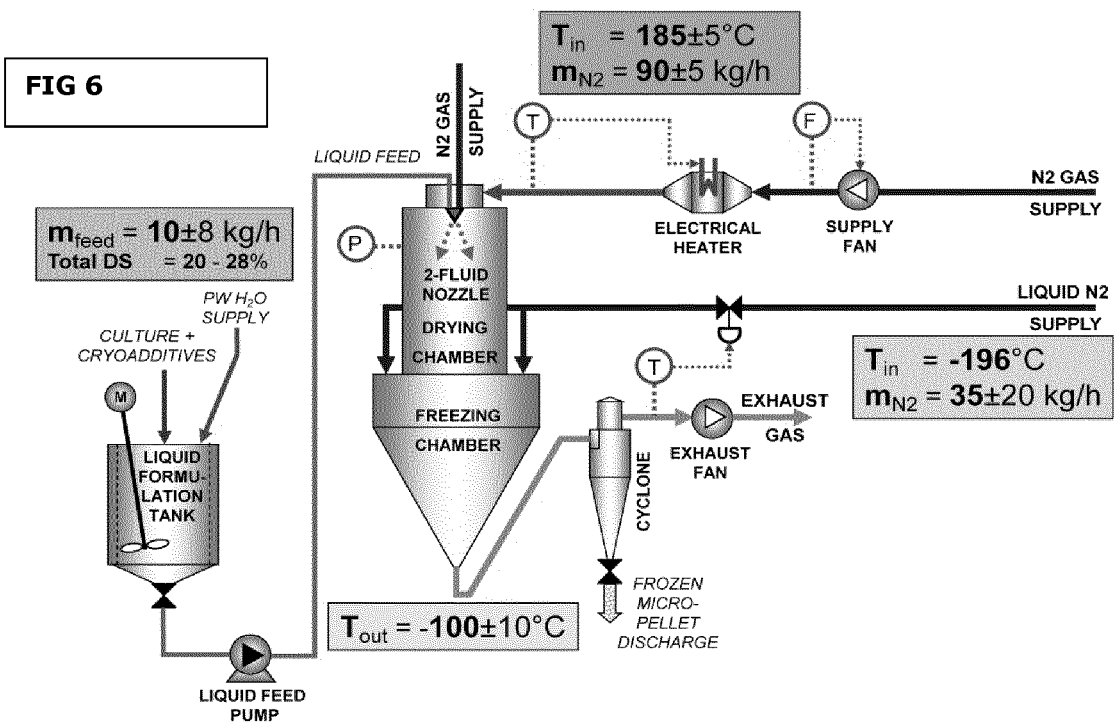

1. Drying gas supply
2. Supply fan
3. Heater
4. Cryogenic gas supply
5. Nozzle (with optionally gas supply shown)
6. Liquid feed
7. Liquid feed tank
8. Protein or Microorganism suspension, optional with cryoprotectant
9. Water inlet
10. Liquid feed pump
11. Drying chamber
12. Freezing chamber
13. Frozen powder discharge
14. Cyclone
15. Exhaust fan
16. Exhaust gas
T. Temperature regulator
P. Pressure regulator
F. Drying gas regulator FIGS. 5 and 6 depicts preferred embodiments of the apparatus

EXPERIMENTAL

Example 1

A sample of 1281 g of *Streptococcus thermophilus* (strain ST-Fe 2) concentrate was kept at <5° C. This contained 1.7E+11 CFU/g with approx. 12.8% (w/w) dry solids. Parallel to this 579 g of solution was prepared by adding the following ingredients to 470 g of cold tap water (approx. 10° C.) under agitation: 33 g sodium ascorbate, 32 g sodium caseinate, 22 g inositol and 22 g monosodium glutamate (MSG).

The sample and the additive solution were mixed. This resulted in 1.86 kg of liquid formulation with approx. 14.6% (w/w) dry solids to be spray dried. This liquid formulation contained now approx. 1.2E+11 CFU/g and was kept cold (<5° C.) throughout the test.

A GEA Niro Mobile Minor laboratory spray dryer was modified to accommodate spray drying using two 380 mm top extension sections followed by liquid nitrogen injection in the lower fixed section of the standard spray chamber to accommodate in-situ freezing of the partially dehydrated product droplets arriving from the upper section of the chamber. The upper spray drying section was supplied with heated pure nitrogen drying gas and the lower freezing section was supplied with liquid nitrogen capable of generating a frozen particulate colder than −100° C.

The upper spray dryer section inlet temperature was kept at 190° C., using a nitrogen drying gas kept at a mass flow-rate of approx. 100 kg/h. A 2-fluid nozzle (Schlick 0-2) was used for the atomization of the above mentioned liquid formulation, using an atomization gas flow of approx. 5 kg/h (Nitrogen) equivalent to an atomization pressure of 0.8 Bar(g)

The liquid formulation was sprayed into the upper spray dryer section. The feed-rate was kept at 2 kg/h and the spray drying/freezing chamber outlet temperature was kept in the range −140 to −110° C.

A free-flowing frozen powder with an average particle size of 105 micron was collected below the downstream cyclone. After 55 min. about 1100 g of partially dehydrated frozen formulation has been collected, which corresponds to a yield of about 70%. The moisture content was now 18.5% (w/w) measured as total volatiles on a Sartorious IR at 115° C. This corresponds to a reduction of the total water amount in our product of approx. 24% (w/w).

The obtained partially dehydrated frozen powder contained now 1.5E+11 CFU/g. The frozen powder was freeze dried, performed at a chamber pressure of 0.3 mbar with temperature increasing from −42° C. to 32° C. with 1.5° C./min. The freeze drying was ended when the weight of the product has been constant/stable for at least 2 hours. The dried product had an acceptable stability after 3 months storage at 5° C. (pH 5.6 as measured using standard CINAC analysis).

Example 2

Example 1 was repeated using the same equipment, conditions and additive solution, but with the strain ST-4895. Thus a sample of 1281 g *Streptococcus thermophilus* strain ST-4895 concentrate was mixed with 579 g of additive solution, resulting in 1.86 kg of liquid formulation with approx. 14.6% (w/w) dry solids to be spray dried. This liquid formulation contained now approx. 1.2E+11 CFU/g. After drying and freezing, a frozen powder was obtained.

Figure 3:
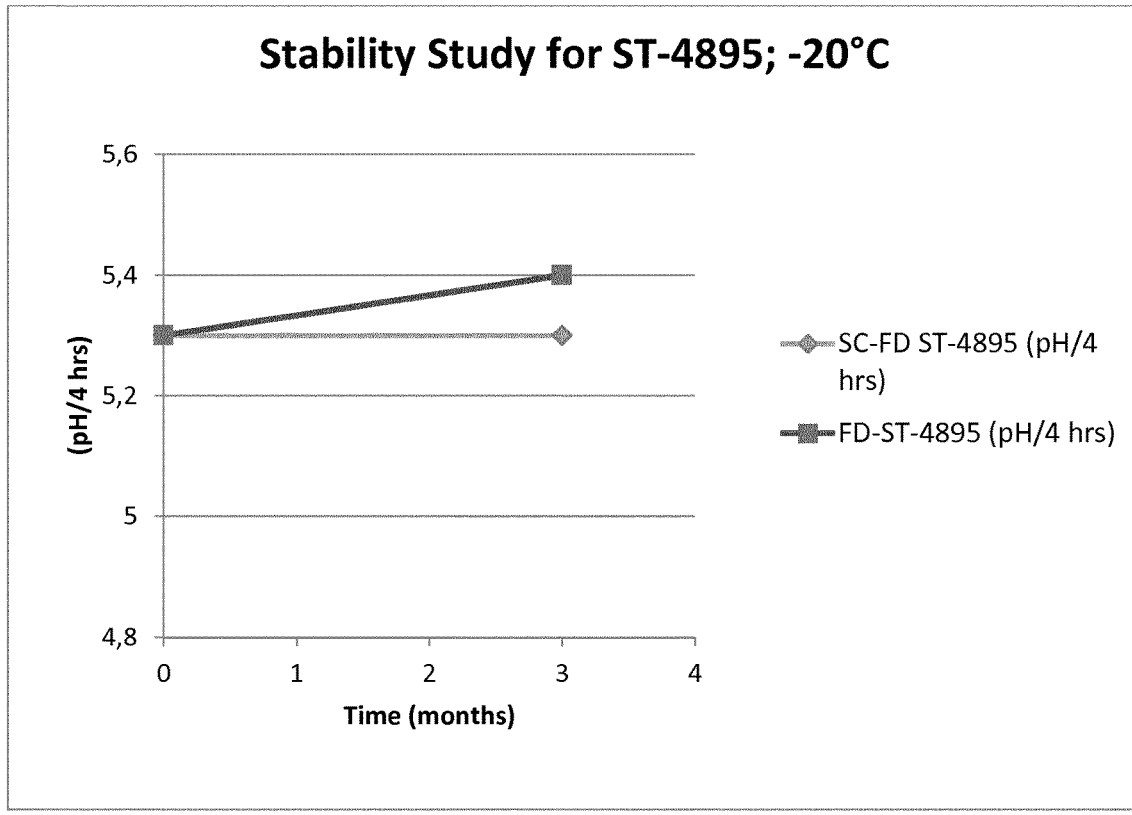
FIG. 3 depicts the stability data for the strain ST-4895 after 3 months storage at −20° C. and at +5° C., cf. example 2.
Figure 3:
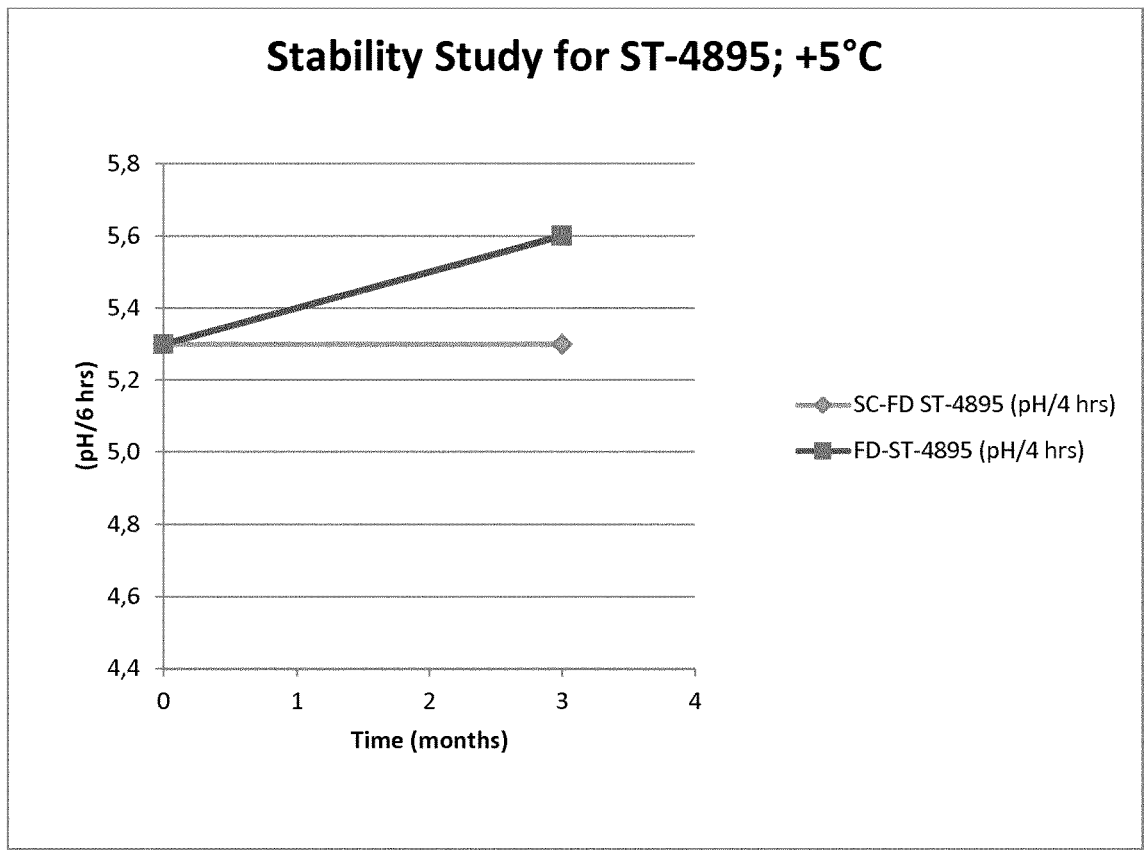
Figure 4:
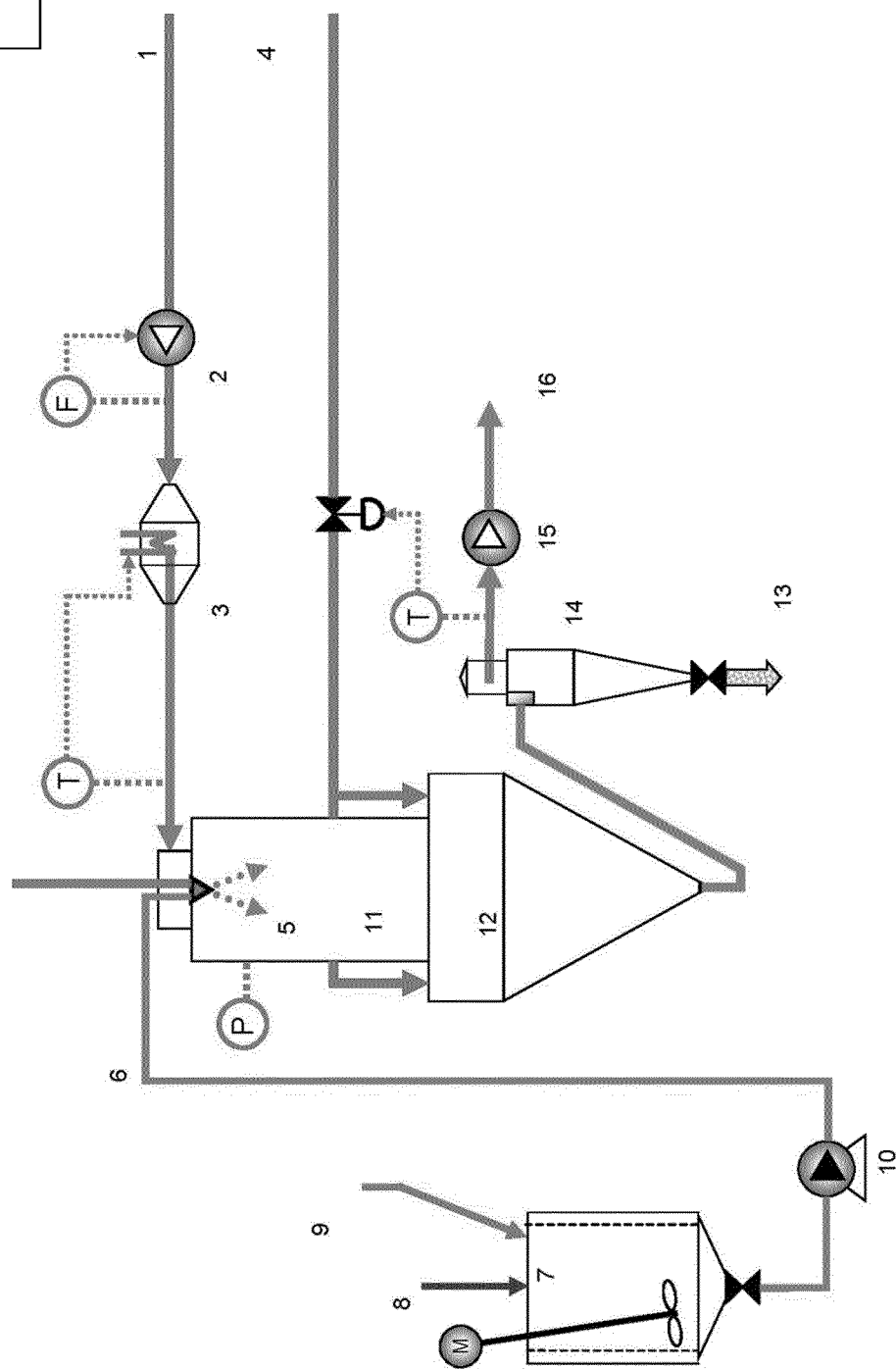
FIG. 4 depicts a spray drying/freezing apparatus according to the invention

The spray-frozen powder was freeze dried (cf. example 1). The stability of the dried product was compared with a freeze-dried product obtained from a "standard" pellet-frozen concentrate of ST-4895. Performance of the freeze dried products was examined by using standard CINAC analysis. For three months stability data, see FIG. 3. The

Example 3

Example 1 was repeated using the same equipment, conditions and additive solution, but with the *Streptococcus thermophilus* strain ST-143. Thus, a sample of 1281 g of *Streptococcus thermophilus* (strain ST-143) concentrate was mixed with 579 g of additive solution. This resulted in 1.86 kg of liquid formulation with approx. 14.6% (w/w) dry solids to be spray dried. This liquid formulation contained now approx. 1.2E+11 CFU/g. After drying and freezing, a frozen powder was obtained.

Example 4

Example 1 was repeated using the same equipment, conditions and additive solution, but with the *Streptococcus thermophilus* strain ST-44. Thus, a sample of 1281 g of strain ST-44 concentrate was mixed with 579 g of additive solution.

This resulted in 1.86 kg of liquid formulation with approx. 14.6% (w/w) dry solids to be spray dried. This liquid formulation contained now approx. 1.2E+11 CFU/g. After drying and freezing, a frozen powder was obtained.

Figure 1:
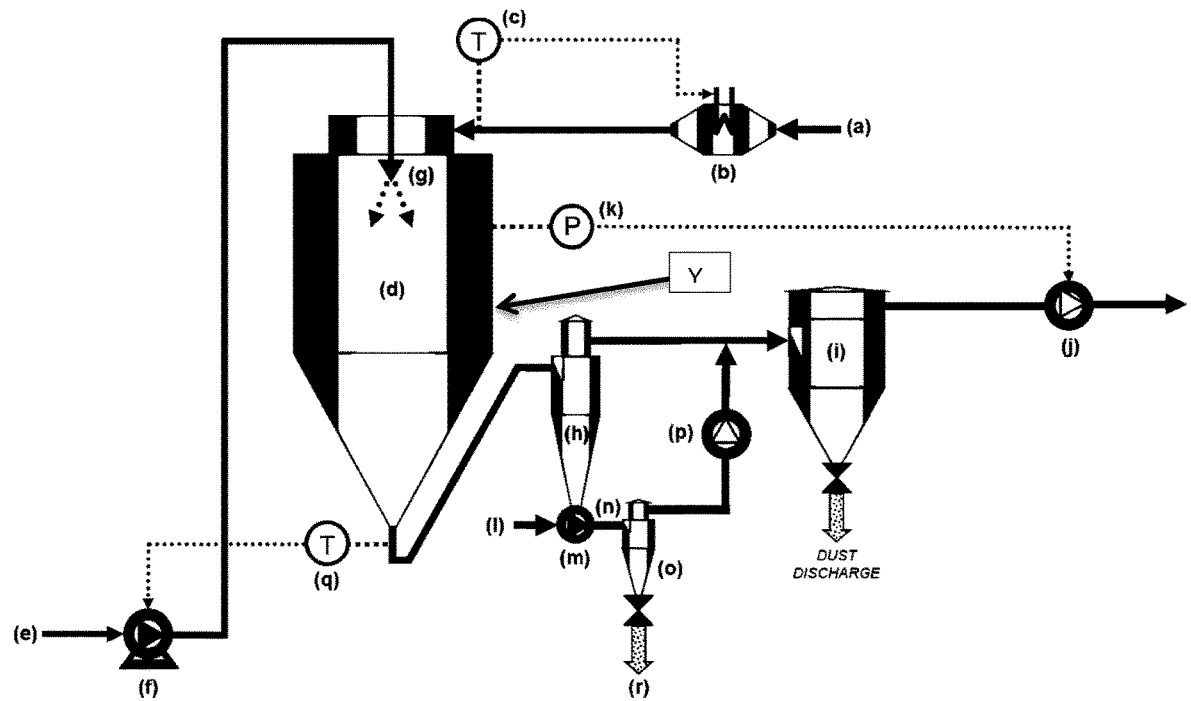
Figure 2:
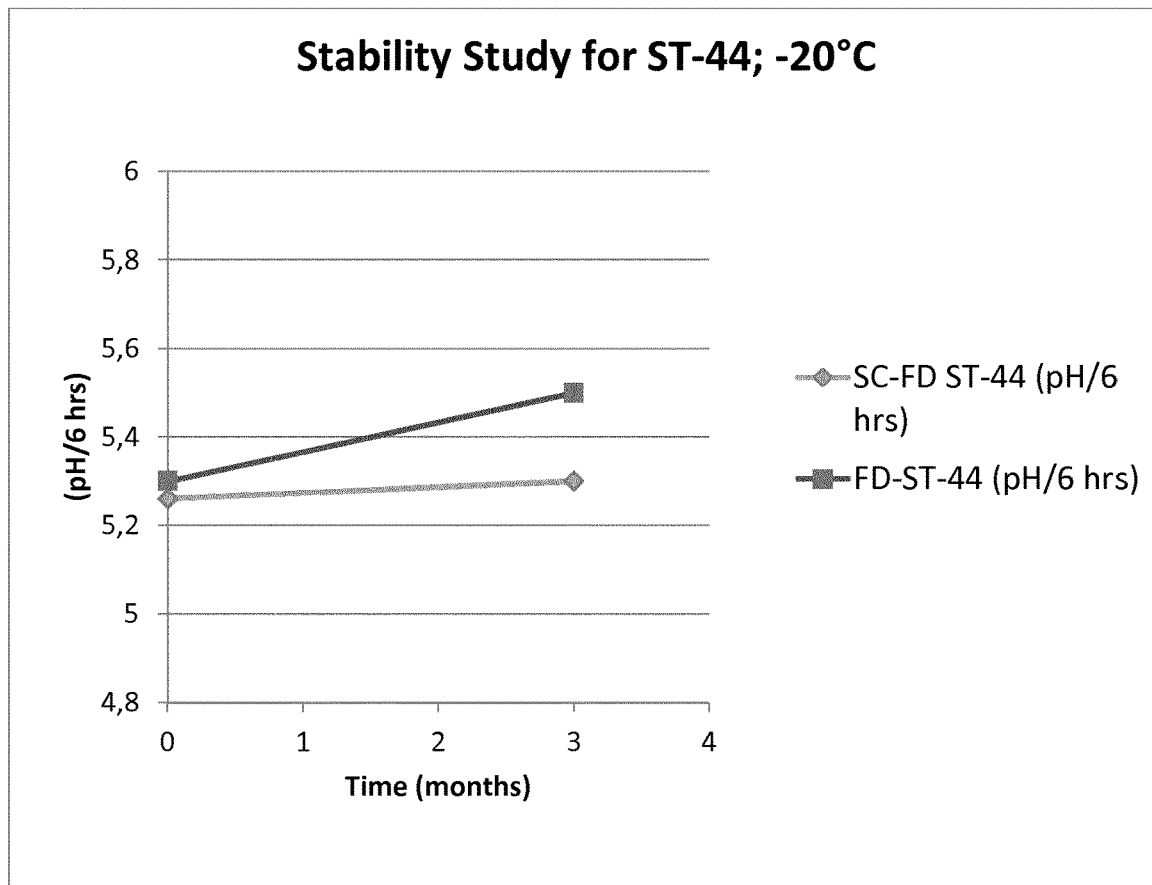
Figure 2:
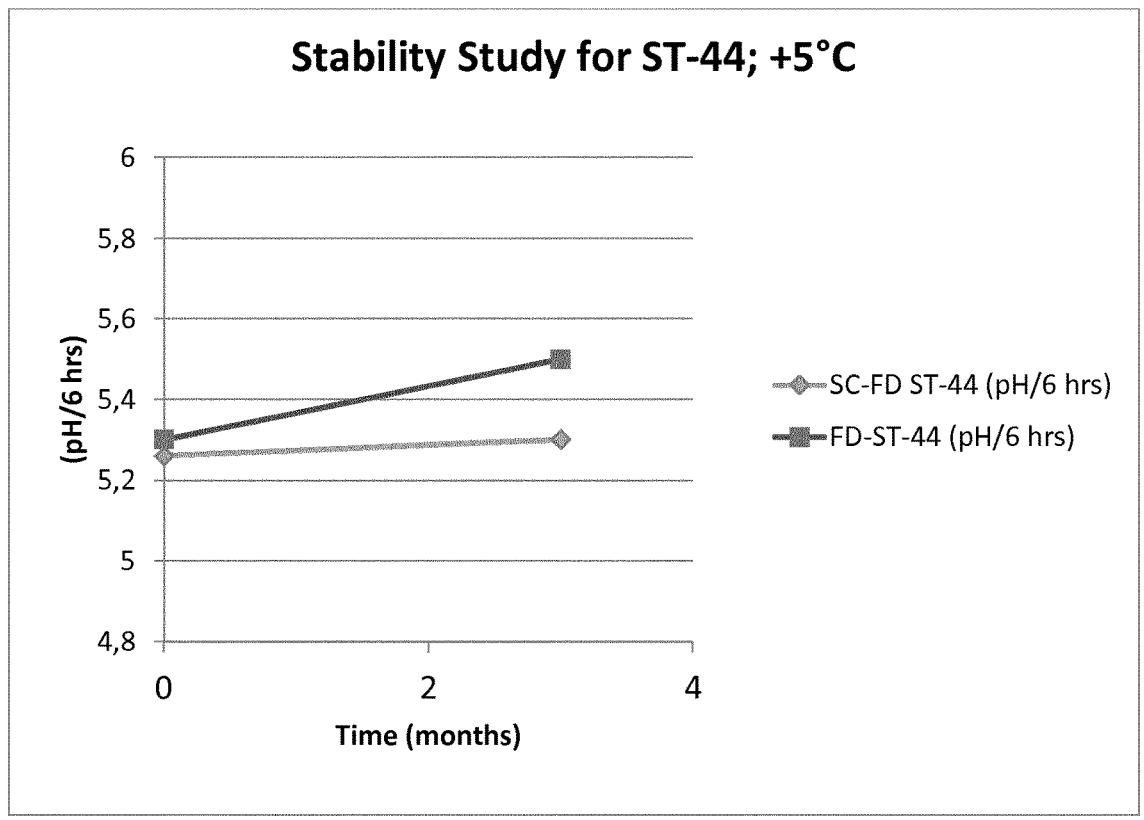

The spray-frozen powder was freeze dried as in example 1, and the stability of the dried product was compared with a product obtained by freeze drying a pellet-frozen concentrate of ST-44 (method as in example 2). For three months stability data, see FIG. 2. The product produced according to the present invention is stable, even if compared to the pellet-frozen product.

Example 5

A sample of 2640 g of *Bifidobacterium animalis* ssp. *lactis* (strain BB-12®) concentrate was kept at <5° C. This contained 2E+11 CFU/g with approx. 14.5% (w/w) dry solids. Parallel to this 1080 g of solution was prepared by adding the following ingredients to 876 g of cold tap water (approx. 10° C.) under agitation: 60 g sodium ascorbate, 79 g skimmed milk powder, 33 g inositol and 33 g MSG. The sample and the additive solution were mixed. This resulted in 3.72 kg of liquid formulation with approx. 15.7% (w/w) dry solids to be spray dried. This liquid formulation contained now approx. 1.4E+11 CFU/g and was kept cold (<5° C.) throughout the test. After drying and freezing preformed as in example 1, a frozen powder was obtained. The frozen powder was freeze dried, and the dried product had an acceptable cell count after 3 months storage at 5 C (2.9E+11 CFU/g).

Example 6

A sample of 1145 g of *Lactobacillus bulgaricus* (strain LB CH-2) concentrate was kept at <5° C. This contained 1.1E+11 CFU/g with approx. 11.5% (w/w) dry solids. Parallel to this 375 g of solution was prepared by adding the following ingredients to 282 g of cold tap water (approx. 10° C.) under agitation: 27 g sodium ascorbate, 36 g skimmed milk powder, 15 g inositol and 15 g MSG. The sample and the additive solution were mixed. This resulted in 1.52 kg of liquid formulation with approx. 14.7% (w/w) dry solids to be spray dried. This liquid formulation contained now approx. 8.5E+10 CFU/g and was kept cold (<5° C.) throughout the test. After drying and freezing preformed as in example 1, a frozen powder was obtained. The frozen powder was freeze dried, and the dried product had an acceptable stability after 3 months storage at 5 C (pH 6 as measured using standard CINAC analysis).

REFERENCES

EP1234019B1 (Danisco A/S)
U.S. Pat. No. 6,010,725A (Nestle SA)
Semyonov et al (Food Research International 43, 193-202 (2010)
U.S. Pat. No. 7,007,406 (Wang)
WO15063090A2, WO14029758A1, WO14029783A1 (Chr Hansen A/S)
ISO 13320:2009 standard for *Particle size analysis—Laser diffraction methods*

All references cited in this patent document are hereby incorporated herein in their entirety by reference.

The invention claimed is:

1. A process for removing liquid from a solution or suspension containing microorganisms, comprising:
    (a) preparing droplets of a solution or suspension containing microorganisms by spraying the solution or suspension;
    (b) spray-drying the droplets by contacting the droplets with a drying gas;
    (c) freezing the droplets obtained in step (b) with a cryogenic gas to obtain a frozen product; and
    (d) freeze-drying the frozen product under reduced pressure to a water activity ($a_w$) below 0.20, to produce a freeze-dried product.

2. The process of claim 1, wherein the microorganisms comprise lactic acid bacteria (LAB).

3. The process of claim 2, wherein:
    spray-drying step (b) comprises spraying an aqueous suspension containing the LAB into a drying gas in a spray chamber; and
    freezing step (c) comprises contacting the product resulting from step (b) with a cryogenic gas in a chamber to obtain a frozen powder as the frozen product.

4. The process of claim 2, wherein:
    spray-drying step (b) comprises spraying a liquid suspension containing the LAB into a chamber containing a drying gas; and
    freezing step (c) comprises freezing the droplets resulting from step (b) by contacting the droplets with a cryogenic gas in a chamber to obtain a frozen suspension as the frozen product.

5. The process of claim 1, wherein the spraying of step (a) is carried out by passing the solution or suspension through a spray nozzle or a rotating atomizing device, wherein the spray nozzle or rotating atomizing device results in droplets having a size of from 10 to 500 micrometers, measured as Dv90 values in micrometers.

6. The process of claim 1, wherein the frozen product is collected by a cyclone having a maximum differential pressure drop across the cyclone of about 100 mm water column, or an electrostatic filter.

7. The process of claim 1, wherein the spray-drying step (b) and freezing step (c) are independently conducted at a pressure in the range of from 60 to 200 kPa.

8. The process of claim 1, wherein spray-drying step (b) is conducted with a retention time of less than 2 minutes in a spray dryer, and wherein the resulting product is directly introduced into a freezing chamber.

9. The process of claim 1, wherein spray-drying step (b) is carried out with a drying gas inlet temperature of at most 300° C.

10. The process of claim 1, wherein spray-drying step (b) is conducted at a temperature in the range from 20° C. to 250° C.

11. The process of claim 1, wherein, after spray-drying step (b), the droplets have a size of between 20 and 400 microns measured as Dv90 values.

12. The process of claim 1, wherein, after spray-drying step (b), the liquid content of the droplets is reduced by at least 5% by weight as compared to the liquid content of the starting suspension or solution.

13. The process of claim 12, wherein, after spray-drying step (b), the liquid content of the droplets is between 20% and 85% by weight of the total weight of the droplets.

14. The process of claim 1, wherein the drying gas and the cryogenic gas each independently contain less than 5% oxygen.

15. The process of claim 1, wherein the drying gas and the cryogenic gas are independently selected from the group consisting of an inert gas, a noble gas, carbon dioxide, an alkane gas, and mixtures of two or more thereof.

16. The process of claim 1, wherein the cryogenic gas has an inlet temperature in the range of from −50 to −250° C., and/or the cryogenic gas has a temperature of between −20° C. and −150° C. during the freezing step.

17. The process of claim 1, wherein the solution or suspension further comprises an additive selected from inositol, lactose, sucrose, trehalose, inulin, maltodextrin, skimmed milk powder, yeast extract, casein peptone, inosine, inosinemonophospate, glutamine and salts thereof, casein and salts thereof, ascorbic acid and salts thereof, and polysorbate.

18. The process of claim 17, wherein the ratio of microorganisms to additive is from 1:0.1 to 1:10 (w/w of the dry weights).

19. The process of claim 1, wherein the microorganisms are selected from a yeast, a *Streptococcus* species, a *Lactobacillus* species, a *Lactococcus* species, a *Leuconostoc* species, a *Bifidobacterium* species, an *Oenococcus* species, and a *Bacillus* species.

20. The process of claim 1, wherein the process is carried out in an apparatus comprising a two-chamber tower, the tower comprising:
a first (upper) chamber comprising (i) an atomizer adapted to atomize the suspension or solution, and (ii) an inlet for the drying gas; and
a second (lower) chamber comprising (iii) an inlet for the cryogenic gas, and (iv) an outlet coupled to a cyclone;
wherein the drying gas having a temperature in the range from 20° C. to 250° C. and the suspension or solution are sprayed into the first (upper) chamber, and the cryogenic gas having a temperature in the range of from −50 to −250° C. is sprayed into the second (lower) chamber.

21. The process of claim 1, wherein the process is carried out in an apparatus comprising a chamber having (i) an atomizer for atomizing the solution or suspension, (ii) an inlet for the drying gas, (iii) an inlet for the cryogenic gas, and (iv) an outlet.

22. The process of claim 1, further comprising packaging the freeze-dried product.

23. The process of claim 21, wherein the inlet for the drying gas is integrated in the atomizer.

24. The process of claim 21, wherein the outlet is connected to a cyclone.

25. A product obtained by the process of claim 1.

26. The product of claim 25, packaged in an airtight container.

* * * * *